US012766090B2

(12) United States Patent
Danoux et al.

(10) Patent No.: US 12,766,090 B2
(45) Date of Patent: Oct. 20, 2026

(54) **COSMETIC USES OF A *HIPPOPHAE RHAMNOIDES* CAKE HYDROLYSATE**

(71) Applicant: BASF Beauty Care Solutions France SAS, Lyons (FR)

(72) Inventors: Louis Danoux, Essey-les-Nancy (FR); Florence Henry, Essey-les-Nancy (FR); Solène Mine Gensollen, Essey-les-Nancy (FR); Philippe Moser, Essey-les-Nancy (FR)

(73) Assignee: BASF BEAUTY CARE SOLUTIONS FRANCE SAS, Lyons (FR)

( * ) Notice: Subject to any disclaimer, the term of this patent is extended or adjusted under 35 U.S.C. 154(b) by 462 days.

(21) Appl. No.: 18/266,822

(22) PCT Filed: Dec. 13, 2021

(86) PCT No.: PCT/FR2021/052285

§ 371 (c)(1),
(2) Date: Jun. 13, 2023

(87) PCT Pub. No.: WO2022/129750

PCT Pub. Date: Jun. 23, 2022

(65) Prior Publication Data

US 2024/0050359 A1 Feb. 15, 2024

(30) Foreign Application Priority Data

Dec. 15, 2020 (FR) ....................................... 2013229

(51) Int. Cl.

| | |
|---|---|
| ***A61K 36/185*** | (2006.01) |
| ***A61K 8/9789*** | (2017.01) |
| ***A61Q 5/00*** | (2006.01) |
| ***A61Q 5/12*** | (2006.01) |
| ***A61Q 7/00*** | (2006.01) |

(52) U.S. Cl.

CPC .......... *A61K 8/9789* (2017.08); *A61K 36/185* (2013.01); *A61Q 5/002* (2013.01); *A61Q 5/12* (2013.01); *A61Q 7/00* (2013.01); *A61K 2236/19* (2013.01); *A61K 2236/37* (2013.01); *A61K 2800/805* (2013.01)

(58) Field of Classification Search

None

See application file for complete search history.

(56) References Cited

U.S. PATENT DOCUMENTS

| | | | |
|---|---|---|---|
| 2008/0044370 | A1 | 2/2008 | Goino et al. |
| 2012/0214746 | A1 | 8/2012 | Dal et al. |
| 2019/0336884 | A1 | 11/2019 | Makerri et al. |

FOREIGN PATENT DOCUMENTS

| | | | |
|---|---|---|---|
| CN | 1490036 | A | 4/2004 |
| CN | 1988883 | A | 6/2007 |
| CN | 105063139 | A | 11/2015 |
| CN | 106344463 | A | 1/2017 |
| CN | 108065411 | A | 5/2018 |
| CN | 108354862 | A | 8/2018 |
| EP | 1759683 | A1 | 3/2007 |
| FR | 2943255 | A1 | 9/2010 |
| FR | 2951944 | A1 | 5/2011 |
| FR | 3031455 | A1 | 7/2016 |
| FR | 3061416 | A1 | 7/2018 |
| FR | 3069450 | A1 | 2/2019 |
| WO | 2009/125071 | A2 | 10/2009 |
| WO | 2019/069007 | A1 | 4/2019 |

OTHER PUBLICATIONS

Lin et al. (2022) Food Science and Human Wellness 11: 1028-1035. (Year: 2022).*

Zheng et al. (2025) Food Chemistry: X 102523 (13 pages) (Year: 2025).*

Anonymous, "Restorative Hair Serum," Database Gnpd, Database accession No. 7446557, XP055848347.

International Search Report and Written Opinion received for PCT Patent Application No. PCT/FR2021/052285, mailed on Apr. 22, 2022, 20 pages (8 pages of English Translation and 12 pages of Original Document).

Koskovac et al., "Sea Buckthorn Oil-A Valuable Source for Cosmeceuticals," Cosmetics, vol. 4, No. 40, Oct. 16, 2017, pp. 1-10.

Lian et al., "Study on antioxidant activity of peptide fractions from seabuckthorm seed enzymatic hydrolysates", Science and Technology of Food Industry, issue 22, 2013, 12 Pages (8 pages English Translation and 4 pages Original Copy).

* cited by examiner

*Primary Examiner* — Russell G Fiebig

(74) *Attorney, Agent, or Firm* — Faegre Drinker Biddle & Reath LLP

(57) ABSTRACT

The invention relates to the cosmetic use of a *Hippophae rhamnoides* cake hydrolysate for increasing the growth of skin appendages and/or reducing loss thereof; increasing their biomechanical properties and/or their surface and/or textural properties; and/or repairing damaged skin appendages. The invention also relates to a cosmetic care method comprising the topical application of the cake hydrolysate or a cosmetic composition containing same. The invention also relates to an *H. rhamnoides* cake hydrolysate or a dermatological or pharmaceutical composition comprising same for dermatological or pharmaceutical use in the treatment of alopecia and/or baldness.

10 Claims, No Drawings

COSMETIC USES OF A *HIPPOPHAE RHAMNOIDES* CAKE HYDROLYSATE

CROSS-REFERENCE TO RELATED APPLICATIONS

This application is a National stage application (under 35 U.S.C. § 371) of PCT/FR2021/052285, filed Dec. 13, 2021, which claims benefit of French Application No. FR2013229, filed Dec. 15, 2020, both of which are incorporated herein by reference in their entirety.

TECHNICAL FIELD

The invention relates to novel cosmetic uses of a *Hippophae rhamnoides* cake hydrolyzate.

PRIOR ART

The care of skin appendages such as the hair, the eyelashes and the eyebrows involves a global treatment, i.e. direct treatment of the hair fiber or keratin fiber but also of the corresponding skin area, including the hair follicles. In the case of the hair, these hair follicles are distributed throughout the scalp and are responsible for hair growth. These follicles contain cells of proliferative epithelial origin in the lower part of the follicle, at the bulb. In addition, the direct care of the hair fiber involves treatment of its constituent proteins. Keratins, for example, are particularly sensitive to damage caused by the urban lifestyle, the frequency of use of chemical hygiene products, styling habits and also environmental conditions, i.e. sun, pollution, salt, wind, variations in climatic conditions, lifestyle in general and also age. These proteins become denatured and make the skin appendages, in particular the hair, less resistant, less supple, brittle, but also duller and with more split ends. These appendages lose their biomechanical and surface properties.

One solution is to supply exogenous proteins to compensate for the damage to the hair proteins.

Hydrolysis (chemical, thermal or enzymatic) is a necessary process, however, in order to break down the proteins to a low molecular weight, promote their solubility in water and in this case their penetration into the hair fiber, making them usable in cosmetic formulations. Only low molecular weight molecules can penetrate the fiber, in particular damaged hair fibers. These hydrolyzed proteins help to improve moisture retention, elasticity of the hair fibers and provide more softness, sheen, bounce and body. They help strengthen the hair fiber from within.

High-performance hydrolyzed proteins have substantive properties for the hair fiber (weak bonds with hair keratins) due to ionic charges and polar sites (interactions by van der Waals forces). They can also form protective films on the surface of the hair fiber.

Products based on hydrolyzed proteins exist on the cosmetic market. These proteins are of plant or animal origin. The most common are hydrolyzed proteins from wheat, silk, keratin, collagen, elastin, milk and almonds. However, there is a constant need for alternative ingredients that are efficient in this field.

Entirely unexpectedly, the inventors found that a hydrolyzate of *H. rhamnoides* cake has the ability to penetrate the keratin fiber, to increase its mechanical properties, and also its texture and surface properties. This hydrolyzate has been shown to be capable of increasing the growth of skin appendages, to fight against their loss, to increase their resistance and to reduce their breakage, in particular that of the hair, making it more shiny, more radiant and with volume. In addition, *H. rhamnoides* cake hydrolyzate has skin appendage repair properties as will be shown in the following description.

One advantage of the hydrolyzate according to the present invention is that it is a product derived from an industrial extraction residue which is usually not upgraded, the development of the product thus falling within an eco-responsible approach. Another advantage is that it is an ingredient providing complete care, as it has effects both on the keratin fiber, in particular the hair, but also on the scalp and the hair follicles. In addition, the hydrolyzate according to the invention can be easily produced on an industrial scale. Finally, enzymatic hydrolysis makes it possible to fractionate the proteins of the cake to recover low molecular weight peptides, the very ones that can penetrate the keratin fibers to provide the cosmetic effects described herein.

The hydrolyzate according to the invention comes from the cake of the *Hippophae rhamnoides* plant. This plant, also called sea buckthorn, is known for its historical uses. Thus, in ancient Greece, its leaves were used as animal feed, in particular for horses to increase the sheen of their coat. The Greeks also used the berries therapeutically for reducing pain and stomach aches and for treating scurvy. Leaf extracts were also used for treating asthma, gastric ulcers, skin problems (scarring, burns) and lung problems. In China, the fruit of *H. rhamnoides* is used for relieving coughs and transforming phlegm, strengthening the stomach and relieving difficult digestion, activating the blood and dispelling stasis. In Central Asia, local people used sea buckthorn for treating hypertension, and digestive and skin disorders. The oil extracted from the berries is used for its anti-inflammatory properties and for treating gastric ulcers. The decoction of the dried fruit is used for skin problems.

Moreover, *H. rhamnoides* extracts already exist on the cosmetic market. Thus, an aqueous extract of the coproduct from the supercritical $CO_2$ extraction of *H. rhamnoides* seeds is sold by the Applicant under the name RNAge™ for its antiaging properties on skin and mucous membranes and was described in patent application WO 2019/069007. However, the extract according to the present invention is different from the latter since it is a hydrolyzate of the coproduct from the supercritical $CO_2$ extraction of the seeds. The cosmetic effects described in the present invention are, moreover, different.

Patent applications CN105063139 and CN108065411 disclose peptide hydrolyzates from the residue of supercritical $CO_2$ extraction of *H. rhamnoides* seeds. These are hydrolyzates obtained by enzymatic hydrolysis. However, neither of these two patent applications disclose the cosmetic or dermatological applications forming the subject of the present invention.

Patent application CN108354862 describes a composition comprising, inter alia, an oil of *H. rhamnoides*, for an antidandruff and soothing effect.

However, firstly this is an oil and not a hydrolyzate, and secondly the cosmetic effects described in the present invention are different from the antidandruff effect of said patent application.

Patent application FR3031455 describes several molecules that can be extracted from *H. rhamnoides* and that are intended to be incorporated into a cosmetic composition notably as a repairing agent, inter alia for the hair. However, no disclosure or suggestion of the precise effects described in the present invention is mentioned. Moreover, an extract of the plant *H. rhamnoides* is disclosed without further description of the type of extract.

Patent application FR2943255 describes the use of an extract of *H. rhamnoides* oil obtained by supercritical $CO_2$ extraction for stimulating the activity of α-5-reductase, in order to improve the loss of hair sheen. However, this is the supercritical $CO_2$ extraction product, not its coproduct, let alone the hydrolyzate thereof. Moreover, the cosmetic effects described in the present patent application are neither disclosed nor suggested.

Patent application WO 2009/125071 describes several plant extracts obtained from supercritical $CO_2$ extraction coproducts, these coproducts then being subjected to aqueous-alcoholic extraction or extraction notably with a mixture of water and butylene glycol. An extract of *H. rhamnoides* fruit is disclosed. However, the extract of the present invention is different since it is a hydrolyzate of the *H. rhamnoides* coproduct. Said patent application also does not at all describe the cosmetic effects described in the present invention and in particular does not describe any effect on the skin appendages.

Thus, to the Applicant's knowledge, no prior art discloses the cosmetic or pharmaceutical uses of the hydrolyzate according to the present invention. Nor are said uses suggested in any document alone or in combination.

DISCLOSURE OF THE INVENTION

A first subject thus relates to the nontherapeutic cosmetic use of a hydrolyzate of *H. rhamnoides* cake for increasing the growth of skin appendages and/or decreasing the loss thereof, advantageously of the hair; and/or for maintaining and/or increasing the biomechanical properties and/or the surface and/or textural properties of the skin appendages, advantageously of the hair; and/or for repairing damaged skin appendages, advantageously the hair.

A second subject relates to the nontherapeutic cosmetic use of the hydrolyzate in a cosmetic composition.

A third subject relates to a nontherapeutic cosmetic care process comprising the topical application of the hydrolyzate according to the invention or of a cosmetic composition comprising same.

A fourth subject relates to a cosmetic treatment method and a final subject relates to the hydrolyzate according to the invention for its dermatological or pharmaceutical use.

A first subject thus relates to the nontherapeutic cosmetic use of a hydrolyzate of *H. rhamnoides* cake for increasing the growth of the skin appendages and/or decreasing the loss thereof, advantageously of the hair; and/or for maintaining and/or increasing the biomechanical properties and/or the surface and/or textural properties of the skin appendages, advantageously of the hair; and/or for repairing damaged skin appendages, advantageously the hair.

The term "cosmetic use" means a use which is neither therapeutic, nor pharmaceutical nor dermatological, i.e. which does not require therapeutic treatment and which is intended for healthy skin and/or skin appendages and/or mucous membranes. The term "healthy" refers to skin or skin appendages or mucous membranes described as nonpathological by a specialist in the field, a dermatologist, i.e. which does not exhibit any infection, inflammation, scar, skin disease or skin condition such as candidiasis, impetigo, psoriasis, eczema, acne or dermatitis, notably seborrheic dermatitis, dandruff, or wounds or injuries and/or other dermatoses and/or alopecia and/or baldness. Thus, for the purposes of the invention, "damaged" skin appendages are appendages that are qualified as nonpathological by a specialist in the field. In particular, damaged skin appendages are appendages that have lost their suppleness and/or elasticity and/or deformability notably and consequently are dehydrated. "Damaged" skin appendages lose their structure and/or visual and/or biomechanical properties. Thus, they become dull and rough, are less resistant, become friable, brittle, split and/or curl and thus have split ends. Moreover, they are rough and are therefore less soft, difficult to style and to shape. This loss of hair surface quality is visible and unsightly. The hair also reflects light less and is thus visibly less shiny and less luminous. The hair is also finer and less thick.

The term "skin appendages" means herein head hair, the eyelashes, the eyebrows, bodily hair, notably beard hair, and/or the nails. According to the invention, the beard includes the moustache. Preferentially, the skin appendages concerned are head hair. The hydrolyzate according to the invention is a topically acceptable ingredient. The term "topically acceptable" means an ingredient that is suitable for topical application, which is nontoxic, non-irritant to the skin, in particular the scalp, or to mucous membranes or the skin appendages, which does not induce an allergic or inflammatory response, and which is not chemically unstable.

The hydrolyzate may be used orally or topically. Advantageously, it is used topically. The term "topically" means the direct local application and/or spraying of the ingredient onto the surface of the skin and/or the mucous membranes and/or the skin appendages, in particular the skin appendages. According to a very advantageous mode, the topical route excludes application to the skin, including the scalp and/or the mucous membranes. The hydrolyzate may be applied topically to all or part of the skin of the body and/or face chosen from the scalp, the legs, the thighs, the arms, the midriff, the neckline, the neck, all or part of the face, the forehead, the chin, the lips, the lip contour, the eye contour, the "T" area of the face, and advantageously the scalp, and/or to all or part of the skin appendages, advantageously to the nails, head hair, bodily hair, notably beard hair, the eyelashes and/or the eyebrows, even more advantageously to head hair, more preferentially head hair.

The term "skin" thus also means the scalp.

A subject of the invention thus relates to the nontherapeutic cosmetic use of a hydrolyzate of *H. rhamnoides* cake for increasing the growth of the skin appendages and/or decreasing the loss thereof, advantageously of the hair; and/or for maintaining and/or increasing the biomechanical properties and/or the surface and/or textural properties of the skin appendages, advantageously of the hair; and/or for repairing damaged skin appendages, advantageously the hair.

For the purposes of the invention, the term "maintaining and/or increasing the biomechanical properties" of the skin appendages means maintaining and/or increasing their resistance and/or elasticity and/or deformability, and/or strength, and/or plasticity property, i.e. their brittleness, in particular their response to stretching, and/or their suppleness. These properties may be evaluated ex-vivo by measuring their resistance to tensile forces. These biomechanical parameters, notably those of the hair, may be evaluated in response to stretching and may be measured, for example, by the tensile test (Dia-Stron). The parameters measured may be the elastic modulus (Pa), the elongation at break (%), the breaking strength (gmf), the gradient of the post-yield plastic region (gmf/% elongation) and are normalized relative to the diameter of the skin appendages. This last parameter (gradient) allows measurement of the plasticity of the study material just before breakage. The technique makes it possible to obtain a curve of stress (or force) as a function of the characteristic elongation of the material studied. It is known that an increase in the elongation at break and a decrease in the post-yield gradient may be observed on hair fibers (skin appendages) damaged by oxidation, reduction or ultraviolet irradiation following cleavage of the disulfide bridges into free groups in the cortical domain.

In one embodiment of the invention, “maintaining and/or increasing the biomechanical properties” of the skin appendages means reducing the glycation products (Advanced Glycation End Products or AGEs) which appear during chrono-induced or photo-induced aging notably, but which also appear on a daily basis in response to environmental conditions, in contact with oxidative chemical or physical agents. These glycation products reduce the biomechanical properties of the appendages. Thus, in one embodiment, the hydrolyzate according to the invention is in an amount that is effective for “maintaining and/or increasing the biomechanical properties of the skin appendages” when the percentage of glycation products measured following the oxidation of albumin as a marker protein, in the presence of iron as catalyst and hydrogen peroxide as oxidizing agent, and in the presence of the hydrolyzate according to the invention, is reduced by at least 20%, advantageously by at least 25% and more advantageously by at least 50%, relative to the percentage of glycation products detected under the same conditions but without extract. Advantageously, the skin appendages are the hair. More advantageously, this is a decrease in the glycation products detected in the presence of the hydrolyzate as prepared according to Example 1a) and under the conditions described in Example 3a) (Table 3).

In an alternative embodiment of the invention, “maintaining and/or increasing the biomechanical properties” of the skin appendages means decreasing the degradation of tryptophan measured in the presence of the hydrolyzate according to the invention as a result of oxidation of albumin in the presence of hydrogen peroxide and iron as oxidation catalyst, by at least 30%, advantageously by at least 40% and more advantageously by at least 95%, relative to the percentage of tryptophan degradation measured in the absence of the hydrolyzate according to the invention. Advantageously, the skin appendages are the hair. More advantageously, it is the hydrolyzate as prepared according to Example 1a), under the conditions described in Example 3b) (Table 4).

In another alternative embodiment of the invention, “maintaining and/or increasing the biomechanical properties of the skin appendages” means decreasing the formation of dityrosine, detected in the presence of iron and hydrogen peroxide after oxidation of albumin, by at least 35%, preferentially by at least 55%, in the presence of the hydrolyzate according to the invention. In an advantageous embodiment, the skin appendages are the hair. More advantageously, the hydrolyzate is the hydrolyzate as prepared according to Example 1a), under the conditions described in Example 3c) (Table 5).

In yet another alternative embodiment of the invention, “maintaining and/or increasing the biomechanical properties of the skin appendages” means decreasing the formation of pentosidin, detected in the presence of iron after oxidation of albumin in the presence of hydrogen peroxide, by at least 35%, preferentially by at least 60%, in the presence of the hydrolyzate according to the invention. In an advantageous embodiment, the skin appendages are the hair. More advantageously, the hydrolyzate is the hydrolyzate as prepared according to Example 1a), under the conditions described in Example 3d) (Table 6).

In yet another embodiment of the invention, “maintaining and/or increasing the biomechanical properties of the skin appendages” means decreasing the formation of Schiff bases, glycation intermediates, in the presence of copper and lipoproteins, by at least 11%, advantageously by at least 18%, very advantageously by at least 93%, in the presence of the hydrolyzate according to the invention, versus the amount of said Schiff bases measured under the same conditions without the hydrolyzate. In an advantageous embodiment, the skin appendages are the hair. More advantageously, the hydrolyzate is the hydrolyzate as prepared according to Example 1a), under the conditions described in Example 3d) (Table 7).

The hydrolyzate according to the invention is thus effective and may be used to increase the resistance, elasticity, suppleness, strength and/or plasticity of the skin appendages, and preferentially those of the hair, and is thus capable of decreasing their breakage.

The term “maintaining and/or increasing the surface and/or textural properties” of the skin appendages, advantageously the hair, also means making said skin appendages smoother and/or softer and/or less rough and thus visually more shiny and/or luminous and thus easy to disentangle and/or easy to style and/or easy to shape. These properties may be evaluated by imaging techniques, for example by video-microscopy or electron microscopy, or by sensory tests on locks of hair, performed by external volunteers trained to define their visual or tactile sensations, or by evaluation tests by experts (hairdressers) or self-evaluation by consumer questionnaires. The effectiveness of a product in its formula is evaluated according to perceptible visual or tactile quality criteria of the hair.

In addition, the term “maintaining and/or increasing the growth of skin appendages” means maintaining and/or increasing the amount of DNA in the fibroblasts of the papilla of the hair follicles. In one embodiment, this refers to an increase in the amount of DNA of at least 20%, advantageously of at least 30% and more advantageously of at least 40%, measured in the fibroblasts of the hair papilla in the presence of the hydrolyzate according to the invention compared to the amount of DNA measured in the absence of the hydrolyzate on non-sensitized fibroblasts. Even more advantageously, the hydrolyzate according to the invention is that described in Example 1a), under the measurement conditions as set forth in Example 4 (Table 8).

In an alternative embodiment of the invention, the term “maintaining and/or increasing growth of the skin appendages” means increasing the amount of ATP in the fibroblasts of the papilla of the hair follicles. In one embodiment, this means an increase in the amount of ATP measured in the fibroblasts of the hair papilla in the presence of the hydrolyzate according to the invention, by at least 10%, preferably by at least 15% and even more preferentially by at least 40%, compared to the amount of ATP measured without the hydrolyzate. Even more advantageously, the hydrolyzate according to the invention is that described in Example 1a), under the measurement conditions as set forth in Example 4 (Table 9).

In yet another alternative embodiment of the invention, “maintaining and/or increasing the growth of skin appendages” means maintaining and/or increasing the synthesis of fibroblasts in the papilla of the hair follicles of said appendages. In one embodiment of the invention, this means an increase in the number of fibroblasts in the papilla by at least 10%, preferentially by at least 20%, more preferentially by at least 25%, in the presence of the hydrolyzate according to the invention, compared to the number of fibroblasts measured without the hydrolyzate. Advantageously, it is an increase in the number of fibroblasts measured in the papilla of the hair follicles. More advantageously, this increase is measured in the presence of the hydrolyzate prepared according to Example 1a), under the conditions described in Example 4 (Table 10).

The effect of the hydrolyzate on increasing the growth of skin appendages, in particular the hair, may also be evaluated ex vivo. Thus, in yet another alternative embodiment of the invention, the term "increasing the growth of the skin appendages" means an elongation of the keratin fibers of at least 5%, advantageously of at least 10%, in the presence of the hydrolyzate according to the invention, advantageously in the presence of an agent sensitizing said fibers and slowing down their elongation, in comparison with the elongation of control keratin fibers sensitized with said agent but without hydrolyzate. Advantageously, this concerns the hair. Very advantageously, the sensitizing agent is capsaicin. More advantageously, the hydrolyzate of *H. rhamnoides* cake is that prepared as described in Example 1a), under the conditions set forth in Example 5.

In addition, the term "decreasing the loss of skin appendages" means increasing the amount of DNA in the fibroblasts of the papilla of the hair follicles, when they are sensitized with a dedicated agent. Advantageously thus, there is an increase of at least 25%, advantageously of at least 50% and very advantageously of at least 60%, in the amount of DNA measured in fibroblasts sensitized with capsaicin and in the presence of the hydrolyzate according to the invention, as compared to the amount of DNA measured in the same fibroblasts sensitized with capsaicin and without hydrolyzate. In a particularly advantageous embodiment of the invention, this involves an increase in the amount of DNA measured in the papilla of hair follicles. More advantageously, this increase is measured in the presence of the hydrolyzate prepared according to Example 1a), under the conditions described in Example 4 (Table 8).

In an alternative mode of the invention, "decreasing the loss of skin appendages" means increasing the number of papilla fibroblasts sensitized with capsaicin by at least 20%, preferentially by at least 30%, more preferentially by at least 50%, in the presence of capsaicin and the hydrolyzate according to the invention, as compared to the number of fibroblasts sensitized with capsaicin and without hydrolyzate. In a particularly advantageous embodiment of the invention, this is an increase in the number of fibroblasts measured in the papilla of the hair follicles. More advantageously, this increase is measured in the presence of the hydrolyzate prepared according to Example 1a), under the conditions described in Example 4 (Table 10).

In yet another alternative embodiment of the invention, "decreasing the loss of skin appendages" means increasing the amount of ATP in the fibroblasts of the papilla of the hair follicles, preferentially when they are sensitized with capsaicin. In an advantageous embodiment, this means an increase in the amount of ATP measured in the fibroblasts of the hair papilla, advantageously subjected to sensitization with capsaicin, in the presence of the hydrolyzate according to the invention, of at least 100%, preferentially of at least 130%, measured in the fibroblasts sensitized with capsaicin and in the presence of the hydrolyzate according to the invention, compared with the amount of ATP measured in the same fibroblasts sensitized with capsaicin without hydrolyzate. In a particularly advantageous embodiment of the invention, this involves an increase in the amount of ATP measured in the papilla of the hair follicles. More advantageously, this increase is measured in the presence of the hydrolyzate prepared according to Example 1a), under the conditions described in Example 4 (Table 9).

The properties of increasing the growth of skin appendages, in particular the hair, and also of increasing the biomechanical and/or surface and/or texture properties of the hydrolyzate according to the invention make it an active ingredient for improving the volume, color, sheen and radiance of skin appendages, and in particular of the hair.

The effectiveness of the hydrolyzate according to the invention on the biomechanical properties of the skin appendages, in particular the hair, may moreover be demonstrated by various tests, including tensile strength tests (Diastron), fatigue tests, or repeated styling tests on the hair, making it possible to evaluate its breakage. It is also possible to quantify the hair fibers having split ends. Moreover, these biomechanical properties may be evaluated by measuring the styling force required on dry or wet hair.

In addition, it is possible to evaluate the penetration of the hydrolyzate by directly measuring its distribution in the skin appendages. Advantageously, the distribution of the hydrolyzate is studied on the hair by various imaging and microscopy techniques. More advantageously, Fourier transform infrared spectrometry (FTIR) may be used. Thus, in an advantageous embodiment of the invention, the hair is studied by FTIR after having been cut transversely, after application of the hydrolyzate according to the invention to hair damaged with an oxidizing agent, in comparison with the same hair damaged with the same oxidizing agent without application of the hydrolyzate, or to undamaged hair. The vibrational profiles of the hydrolyzate are then compared to the vibrational profiles of the cut to evaluate the distribution of the product in the hair. More advantageously, the oxidizing agent is hydrogen peroxide.

In addition, the term "repairing damaged skin appendages" means a repairing effect of the hydrolyzate according to the invention on skin appendages damaged by nutritional deficiencies, pollutants chosen from fine particles known as PM2.5 and PM10, metals, for instance copper or iron, heavy metals, climatic and/or environmental conditions such as wind, rain, sudden variations in temperature and humidity, cold, heat, UV, sea salt, chlorine from swimming pools and other physical or chemical agents, including hydrogen peroxide, in particular present in certain shampoos, cosmetic makeup products, hair coloring, bleaching and perming products, varnishes, solvents and household products, mechanical aggression such as brushing, heat from hairdryers and straightening irons, for example, but also intrinsic and/or chrono-induced aging. The latter is indeed also responsible for the loss of structural and/or functional qualities of the skin appendages, including loss of moisture, in particular of the eyelashes, eyebrows and hair which deteriorate.

For the purposes of the present invention, the term "repairing the skin appendages" means at least partially improving the structure and/or visual properties and/or biomechanical properties of the skin appendages, preferentially of the hair. This repair is preferentially evaluated when the skin appendages are exposed to environmental, chemical, biological and/or mechanical stresses.

Environmental stresses notably include smoke, pollution, temperature, notably hot and cold and sudden variations thereof, water content, notably humidity or dryness, solar irradiation, notably the visible spectrum, UV and/or gamma rays, rain, wind, dust and sea salt.

Chemical stresses include harsh household products, chlorine from swimming pools, harsh cosmetic products such as coloring and bleaching products, nail polish and/or removers, solvents, and makeup.

The chemical stresses on the hair in particular include aggressive shampoos and haircare and/or treatment products notably for styling or shaping such as straightening and/or perming, and/or for dyeing and/or bleaching.

The mechanical stresses notably include friction such as brushing and/or rubbing against fabrics (ears, clothes) and/or particles such as dust and/or sand, heating with hairdryers and straightening irons, and/or styling, notably with exposure to pulling, stretching and/or twisting forces.

The hydrolyzate according to the invention is also effective as an antiaging ingredient for the skin appendages, advantageously the hair, and/or the skin, advantageously the scalp, and/or the mucous membranes, by reducing the negative effects of aging.

Thus, in one embodiment of the invention, the restorative effect may be evaluated according to existing techniques in the field. The conventional methods for measuring a repair effect make it possible to measure the ability of the product evaluated to restore a visual, structural and/or functional state of a damaged skin appendage, preferentially of damaged hair, comparable to the state of an undamaged skin appendage, preferentially of undamaged hair. They are applied to damaged skin appendages, preferentially to damaged hair, and the repair effect is measured by comparison with undamaged skin appendages, preferentially undamaged hair.

Advantageously, the repair effect is a repair effect on skin appendages damaged in vitro with an oxidizing agent, which induces denaturing of the proteins of the appendages. Advantageously, it is a repair effect of the hydrolyzate on the hair and the oxidizing agent is more preferentially hydrogen peroxide. More advantageously, this protein denaturing is evaluated by measuring the protein denaturing temperature (° C.) by differential scanning calorimetry (Wortmann and Deutz, *Appl. Polym. Sci.,* 48, 137-150 (1993)) using a differential enthalpy analyzer (DSC Q100, TA Instruments) under the conditions described in Example 6. Thus, the hydrolyzate according to the invention is in an amount effective for repairing the skin appendages, preferentially the hair, when the repair index of the damaged appendages is at least 20%, preferentially at least 30% relative to "healthy" appendages, i.e. appendages that have not been subjected to oxidative stress induced with hydrogen peroxide. Advantageously, this involves measurement of the repair index in the presence of the hydrolyzate as prepared according to Example 1a), under the conditions described in Example 6.

To evaluate in vivo this repair effect on the skin appendages, advantageously the hair, several methods may be used chosen from video microscopy, confocal microscopy, FTIR or Raman microscopy, X-rays, and electron microscopy, the purpose of which is notably to observe the state and/or quality of the cuticle, the protective envelope of the keratin fiber of the skin appendages, by visualizing and quantifying the detached scales as a sign of the surface damage. Physical surface quantification methods for evaluating the morphology of the skin appendages, in particular the hair, such as atomic force microscopy or white-light interferometric profilometry, for evaluating the chemistry (XPS), the charge (streaming potential) or the energy (inverse gas chromatography) may be implemented.

To evaluate the repair effect of the hydrolyzate according to the invention on the internal properties of skin appendages, in particular the hair, calorimetry (DSC) may be used.

The hydrolyzate according to the invention is a hydrolyzate obtained by enzymatic or chemical hydrolysis of the coproduct from the supercritical $CO_2$ extraction of *H. rhamnoides* seeds, i.e. of the coproduct from the oil, or of the coproduct obtained after pressing said seeds. For the purposes of the present invention, the seed corresponds to the berry (or fruit) of *H. rhamnoides* free of the pulpy part, also known as the pericarp. Supercritical extraction with carbon dioxide is a technique which is familiar to those skilled in the art, which allows the isolation of the oily fraction of the compound to be extracted, so it may be used in various applications. For the purposes of the present invention, the residue of this extraction is called the "coproduct" and contains all of the compounds not extracted via said technique. The term "coproduct" thus means the residue obtained after extraction of the oil, also called the cake. The term "cake" will be used in the following description. Advantageously, it is thus the defatted fraction of *H. rhamnoides* seeds. Preferentially, it is the enzymatic or chemical hydrolyzate of the coproduct from the supercritical $CO_2$ extraction of *H. rhamnoides* seeds, more preferentially its enzymatic hydrolyzate. More preferentially, the coproduct does not contain any oil.

The enzymatic hydrolysis may be performed in the presence of any protease known to those skilled in the art, and advantageously in the presence of an enzyme of animal origin chosen from pepsin, enzymes of pancreatic origin such as trypsin or chymotrypsin, and preferentially trypsin, of plant origin chosen from papain, bromelain, ficin or actinidin, preferentially papain, or of bacterial origin chosen from the enzyme from the *Bacillus licheniformis* strain sold under the name Alcalase® or from the strain *B. subtilis*, preferentially Alcalase®. In a particularly advantageous embodiment of the invention, the enzyme used is Alcalase®.

The hydrolysis may be performed at a pH of between 3 and 9 depending on the optimum pH of the enzyme, and advantageously at a pH of between 4 and 8.5, very advantageously at a pH of 8.5. The hydrolysis may be performed at a temperature of from 40° C. to 65° C., advantageously from 50 to 60° C. and very advantageously at 55° C. It is performed over a period of 1 hour to 3 hours and preferentially over a period of 2 hours.

The enzyme used is then inactivated by heating, advantageously at a temperature of from 80° C. to 100° C. and very advantageously at a temperature of 90° C., for a period of from 5 minutes to 30 minutes, preferentially for a period of 10 minutes. The inactivation of the enzyme takes place at a pH of between 5 and 8, preferentially at pH 6.5.

The hydrolyzate obtained is then centrifuged and purified by successive filtrations to a porosity of 0.22 μm.

Advantageously, before the enzymatic hydrolysis step, the proteins are first extracted from the cake. In this case, they are extracted at a pH of between 7.5 and 10, advantageously at a pH of between 8 and 9, very advantageously at a pH of 9.0, for a period of 30 minutes to 2 hours, preferentially for a period of 1 hour.

The weight amount of cake used for the protein extraction and hydrolysis is between 5% and 20%, advantageously between 5% and 15%, more advantageously it is 10% by weight, relative to the total weight of the solvent and the cake.

The solvent used for the protein extraction is chosen from water, coconut water as solvent as described in patent application FR3061416, or a solvent comprising at least 50% by weight, relative to the total weight of the solvent, of at least one $C_6$-$C_{16}$ dialkyl carbonate as described in patent application FR3069450, including a $C_7$-$C_{10}$, advantageously $C_8$, dialkyl carbonate, for example dioctyl carbonate or diethylhexyl carbonate. Advantageously, the solvent used is water as the sole solvent.

Said protein extraction may be performed at a temperature of from 4° C. to 300° C., advantageously from 4° C. to 100° C., more advantageously from 15° C. to 80° C., very advantageously from 15° C. to 30° C., including room temperature, i.e. at a temperature of 20° C. In a particularly advantageous embodiment of the invention, the protein extraction is performed at room temperature.

In an alternative embodiment, the extraction is performed under subcritical conditions.

The term "extraction under subcritical conditions" means extraction in the presence of water, under temperature conditions of greater than 100° C. and pressure conditions of less than 22.1 MPa (221 bar), such that the water remains in the liquid state but has a viscosity and a surface tension lower than that of water at room temperature, increasing its dielectric constant. Thus, the extraction pressure will be between 10 MPa (100 bar) and 25 MPa (250 bar), preferentially between 15 and 22.1 MPa (150 and 221 bar).

Thus, under subcritical conditions, the extraction is performed in water at a temperature ranging from 100° C. to 300° C., advantageously from 120° C. to 250° C., more advantageously between 140° C. and 200° C. The extraction may be performed at a single given temperature or at successive increasing temperatures. In one advantageous embodiment of the invention, the extraction will be performed at a single temperature of 160° C. In an alternative embodiment, it will be performed according to a gradient of three increasing temperatures between 100° C. and 200° C., such as 120° C., 140° C. then 160° C., or 110° C., 130° C. then 150° C., or else 120° C., 145° C. then 170° C. In a particularly advantageous embodiment of the invention, the hydrolyzate is obtained by enzymatic digestion as follows: the proteins are extracted over a period of one hour at room temperature, at pH 12, from an amount of 10% by weight of cake relative to the total weight of cake and water as solvent. The proteins thus extracted are subjected to hydrolysis for a period of 2 hours at a temperature of 55° C. and pH 8.5, in the presence of a 5% volume concentration of Alcalase® relative to the total volume of Alcalase® and protein. The enzyme is inactivated by heating for a period of 20 minutes at a temperature of 90° C. and pH 6.5. The mixture is then cooled, centrifuged and filtered (0.22 μm), under the conditions as described in Example 1a). Alternatively, the proteins of the cake are extracted over a period of one hour at room temperature, i.e. at a temperature of 20° C., at pH 8.5, using an amount of 10% by weight of cake relative to the total weight of cake and water as solvent. The proteins thus extracted are subjected to hydrolysis for a period of 2 hours at a temperature of 55° C. and pH 8.5, in the presence of a 5% volume concentration of Alcalase® relative to the total volume of Alcalase® and protein. The enzyme is inactivated by heating for a period of 20 minutes at a temperature of 90° C. and pH 6.5. The mixture is then cooled, centrifuged and filtered (0.22 μm) under the conditions described in Example 1 b).

Alternatively also, the proteins of the cake are extracted over a period of one hour at room temperature, i.e. at a temperature of 20° C., at pH 12, using an amount of 10% by weight of cake relative to the total weight of cake and water as solvent. The proteins thus extracted are subjected to hydrolysis over a period of 2 hours at a temperature of 55° C. and pH 8.5, in the presence of a 5% volume concentration of papain relative to the total volume of papain and protein. The papain is inactivated by heating for a period of 20 minutes at a temperature of 90° C. and pH 6.5. The mixture is then cooled, centrifuged and filtered (0.22 μm), under the conditions as described in Example 1c).

The hydrolyzate according to the invention consequently comprises a dry matter content of 1% to 20% by weight, advantageously of 2% to 10% by weight, including 5%, a total protein content of 15 g/L to 35 g/L of hydrolyzate, advantageously 18.8 g/L of hydrolyzate and also a percentage of peptides with a molecular weight of from 5 kDalton (Da) to 30 kDa of between 15% and 40%, advantageously 18.25%, a percentage of peptides with a molecular weight of less than 5 kDa of between 40% and 85%, advantageously 72.6% (Example 2). Advantageously, the hydrolyzate comprises a dry matter content of at least 3% by weight, in particular of at least 3.5% by weight, more particularly of 3.44% by weight, very advantageously of 3.84% by weight. In an even more advantageous mode, the hydrolyzate comprises a dry matter content of 5% by weight.

Very advantageously, the hydrolyzate comprises a percentage of peptides with a molecular weight of from 5 kDa to 30 kDa of 18.25%, and a percentage of peptides with a molecular weight of less than 5 kDa of 72.6%. Also very advantageously, the hydrolyzate according to the invention does not contain gallic acid or any of the polymers that are hydrolyzable to gallic acid, or hexahydroxydiphenic acid or any of the polymers that are hydrolyzable to hexahydroxydiphenic acid, or ellagic acid or any of the polymers that are hydrolyzable to ellagic acid, or gallotanins or ellagitanins. More advantageously, the hydrolyzate also does not contain, either, any of the derivatives of the compounds mentioned or any salts thereof, in particular as described in patent application FR031455.

In another advantageous embodiment, the hydrolyzate according to the invention does not contain L-quebrachitol, nor other methyl inositols and/or inositols as described in WO 2009/125071. In particular, the hydrolyzate according to the invention does not contain myricetin, quercetin, kampfaerol or isorhamnetin.

The hydrolyzate, in particular as prepared in Examples 1a) to 1c), is thus in liquid form. Optionally, the hydrolyzate may then be dried for example by freeze-drying or by spraying in the presence of maltodextrins. The hydrolyzate is then in powder form.

In this case, the hydrolyzate according to the invention, in particular obtained under the conditions described in Examples 1a) to 1c), is atomized in the presence of a weight concentration of maltodextrins of between 20% and 90%, preferentially between 40% and 80%, more preferentially from 70% to 80% relative to the total weight of the powder obtained.

The hydrolyzate according to the invention may be used alone or included in a cosmetic composition.

When it is used alone in the form of a cosmetic or dermatological ingredient, it is preferentially dissolved in an aqueous solution containing glycerol, advantageously present in a concentration of from 60% to 90%, more advantageously from 70% to 85%, very advantageously in a concentration of 80% by weight relative to the total weight of the aqueous solution comprising the hydrolyzate.

In one alternative embodiment of the invention, the hydrolyzate will be dissolved and/or diluted in a solvent, notably a polar solvent, such as water, an alcohol, a polyol, a glycol, such as pentylene glycol and/or butylene glycol and/or propylene glycol and/or hexylene glycol and/or caprylyl glycol, or a mixture thereof, preferentially a water-glycol mixture, more preferentially containing a glycol chosen from hexylene glycol, propylene glycol, caprylyl glycol and any mixture thereof. Advantageously, the hydrolyzate obtained is diluted and/or soluble in an aqueous solution containing hexylene glycol, in particular containing between 0.1% and 10% by weight of hexylene glycol, preferentially between 0.5% and 5% by weight of hexylene glycol, relative to the total weight of the cosmetic ingredient. Advantageously, the hydrolyzate obtained is diluted and/or soluble in an aqueous solution containing caprylyl glycol, in particular containing between 0.01% and 5% by weight of caprylyl glycol, preferentially between 0.1% and 1% by weight of caprylyl glycol, relative to the total weight of the aqueous solution comprising the hydrolyzate. Alternatively, the solution in which the hydrolyzate according to the invention is dissolved comprises propylene glycol and caprylyl glycol.

In particular, the aqueous solution in which the hydrolyzate according to the invention is dissolved comprises xanthan gum, in particular between 0.01% and 5% by weight of xanthan gum, relative to the total weight of the aqueous solution, more particularly between 0.1% and 1% by weight of xanthan gum relative to the total weight of the aqueous solution comprising the hydrolyzate.

Advantageously, the solution in which the hydrolyzate according to the invention is dissolved comprises hexylene glycol, caprylyl glycol and xanthan gum.

In an alternative embodiment of the invention, the extract is dissolved in a solution comprising a mixture of sodium benzoate and gluconolactone sold under the name Geogard™.

The hydrolyzate may be incorporated into a cosmetic composition comprising at least one cosmetically acceptable excipient. For the purposes of the present invention, the term "cosmetically acceptable" excipient means a topically acceptable compound and/or solvent, that is to say one which does not induce an undue inflammatory and allergic response on contact with the skin, notably the scalp, which is nontoxic, which is not unstable, or equivalents thereof.

For the purposes of the present invention, the term "cosmetic composition" means a nontherapeutic composition, that is to say a composition intended for preventing and/or for caring for the skin, notably the scalp, and/or skin appendages referred to as "normal" by a dermatologist, that is to say nonpathological. The term "normal" skin or scalp or skin appendage is intended herein to mean a healthy skin or scalp or skin appendage as defined previously.

In a preferential embodiment of the invention, the hydrolyzate according to the invention is present in the cosmetic composition in a content of between $1\times10^{-4}$% to 10% by weight, preferentially from $1\times10^{-4}$% to 5% by weight, more advantageously from $1\times10^{-3}$% to 3% by weight, more preferentially from 0.001% and 0.1% by weight, relative to the total weight of the composition.

The composition may thus be used for increasing the growth of the skin appendages and/or decreasing the loss thereof, advantageously of the hair; and/or for maintaining and/or increasing the biomechanical properties and/or the surface and/or textural properties of the skin appendages, advantageously of the hair; and/or for repairing damaged skin appendages, advantageously the hair.

The cosmetic composition according to the invention may be in the presentation forms conventionally used for topical application to the skin or the scalp and/or skin appendages, preferentially the scalp and/or the skin appendages, such as liquid or solid forms, or even in the form of pressurized liquid. They may be formulated in the form of an aqueous or oily solution, a cream or an aqueous gel or an oily gel, notably in a jar or tube, notably a shower gel, a shampoo, a conditioner, a milk, an oil, an emulsion, a hydrogel, a microemulsion or a nanoemulsion, notably an oil-in-water or water-in-oil or multiple or silicone-based emulsion, a serum, a lotion, notably in a glass or plastic bottle or measuring bottle or an aerosol or spray, a vial, a liquid soap, a paste, a dermatological bar, an ointment, a foam, a mask, a lacquer, a patch, a varnish, an anhydrous product, which is preferably liquid, pasty or solid, for example in the form of a wand, notably in stick form, or in powder form. It may be a makeup product in particular for the eyelashes or the eyebrows such as a mascara or a pencil or a makeup-removing product. In particular, the cosmetic composition is chosen from the group consisting of a serum, a lotion, a cream, a shampoo, a hair conditioner, an oil, a milk, an ointment, a paste, a foam, an emulsion, a hydrogel, a shower gel, a mask, a lacquer, a spray, a wax, a mascara, a makeup pencil or a varnish, advantageously in the form of a shampoo, a conditioner or a lotion.

Preferentially, the hydrolyzate is suitable for the formulation of "neutral and mild" compositions which respect the keratin fiber, notably the hair fiber, and the skin, notably the scalp. The hydrolyzate is also suitable for use in cationic formulations with surfactants.

The compositions according to the invention may contain any suitable solvent and/or any suitable vehicle and/or any suitable excipient, optionally in combination with other compounds of interest. They may notably contain a cosmetically acceptable excipient chosen from surfactants, preserving agents, buffers, swelling agents, chelating agents, biocidel agents, denaturing agents, opacifiers, pH adjusters, reducing agents, stabilizers, emulsifiers, thickeners, gelling agents, film-forming polymers, solvents, fillers, bactericides, odor absorbers, mattifying agents, conditioning agents, texture agents, gloss agents, pigments, colorants, fragrances, chemical or mineral sunscreens, trace elements and essential oils. These combinations are also covered by the present invention. The CTFA Cosmetic Ingredient Handbook, Second Edition (1992) describes various cosmetic ingredients commonly used in the cosmetics industry, which are suitable in particular for topical use on the scalp.

The cosmetic composition may contain other cosmetic agents having properties identical to those of the hydrolyzate according to the invention and inducing an effect which may or may not be synergistic with said hydrolyzate, or may contain cosmetic agents with complementary effects. As hair loss-counteracting active agent, mention will be made of the combination of sulfopeptides, amino acids, aminosaccharides, group B vitamins, zinc and extract of *Panax ginseng* and *Artium majus* sold under the name Trichogen™ LS 8960 by the Applicant or a protective agent for the hair, such as an extract of *Litchi chinensis* pericarp sold under the name Litchiderm™ by the Applicant, or a soothing and anti-itching active agent, such as the rapeseed phytosterols sold under the name Phytosoothe™ LS9766 by the Applicant.

Other active agents may be present in the composition, such as an extract of *Cassia alata* leaves sold under the name DN-Age™ as an antioxidant active agent notably for haircare, a combination of an extract of *Salvia miltiorhizza* and niacinamide sold under the name CollRepair™ as a deglycating agent, or active agents promoting firmness of the skin and thus of the scalp, such as a synthetic tetrapeptide sold under the name Dermican™, an extract of *Hibiscus abelmoschus* sold under the name Linefactor™, a purified pea extract sold under the name Proteasyl™, an extract of

*Manilkara multinervis* sold under the name Elestan™ an extract of *Khaya senegalensis* sold under the name Collalift™ 18, an extract of Argan pulp sold under the name Argassential™ by the Applicant, an extract of *Schizandra chinensis* sold under the name Sgisandryl™, an extract of *Eperua falcate* sold under the name Eperulinen™, or an extract of *Orthosiphon staminus* sold under the name MAT-XS™ Bright sold by the Applicant. These combinations of active agents are notably capable of strengthening the hair follicle and reducing hair loss. The hydrolyzate of the invention may also be combined with a seed extract of the plant *Nephelium lappaceum*, sold under the name Rambuvital™ by the Applicant for its hair-protective properties, notably against pollution.

A third subject of the invention relates to a nontherapeutic cosmetic care process, comprising the topical application of the hydrolyzate according to the invention or of a cosmetic composition comprising same, for increasing the growth of the skin appendages and/or decreasing the loss thereof, advantageously of the hair; for maintaining and/or increasing the biomechanical properties and/or the surface and/or texture properties of the skin appendages, advantageously of the hair; and/or for repairing damaged skin appendages, advantageously the hair.

In an advantageous embodiment of the invention, the cosmetic care process consists of the topical application of the hydrolyzate according to the invention or of the cosmetic composition comprising same to all or part of the skin of the body and/or of the face chosen from the scalp, the legs, the thighs, the arms, the midriff, the neckline, the neck, all or part of the face, the forehead, the chin, the lips, the contour of the lips, the contour of the eyes, the "T" area of the face, and advantageously the scalp, and/or to all or part of the skin appendages, advantageously to the nails, head hair, bodily hairs, notably beard hair, the eyelashes and/or the eyebrows, even more advantageously to head hair, more preferentially to head hair.

The cosmetic care process consequently makes it possible to improve the color and/or sheen and/or radiance and/or volume of the skin appendages, advantageously of the hair.

Yet another subject relates to a cosmetic treatment method for increasing the growth of skin appendages and/or decreasing loss thereof, advantageously of the hair; and/or for maintaining and/or increasing the biomechanical and/or surface and/or textural properties of the skin appendages, advantageously of the hair; and/or for repairing damaged skin appendages, advantageously the hair, and comprising the steps of:

- identifying a dedicated population of humans not suffering from a pathology, notably a skin pathology requiring a therapeutic treatment, for which it is desired to apply the hydrolyzate of *H. rhamnoides* or a cosmetic composition comprising same, and/or who are in need thereof;
- identifying the healthy area of the body and/or the healthy skin, including the healthy scalp, and/or the healthy skin appendage requiring treatment;
- topically applying the hydrolyzate according to the invention or the composition comprising same, in this case in a content of between $1\times10^{-4}$% and 10% by weight, preferentially from $1\times10^{-4}$% to 5% by weight, more advantageously from $1\times10^{-3}$% to 3% by weight, even more preferentially from 0.001% to 0.1% by weight, relative to the total weight of the composition.

A final subject relates to a hydrolyzate of *H. rhamnoides* cake for use, alone or in a dermatological or pharmaceutical composition, which comprises at least one dermatologically or pharmaceutically acceptable excipient, in the treatment of alopecia and/or baldness. In an advantageous embodiment of the invention, the hydrolyzate is as described in the present invention and is present in the dermatological or pharmaceutical composition in a content of between $1\times10^{-4}$% to 10% by weight, preferentially from $1\times10^{-4}$% to 5% by weight, more advantageously from $1\times10^{-3}$% to 3% by weight, more preferentially from 0.001% to 0.1% by weight, relative to the total weight of the composition.

The examples form an integral part of the invention, and any feature appearing to be novel over a prior art, from the description taken in its entirety, including the examples, forms an integral part of the invention. Thus, each example has a general scope.

Unless otherwise indicated, the temperature is expressed in degrees Celsius and the pressure is the atmospheric pressure.

EXAMPLES

Example 1: Various Methods for Preparing the Cake Hydrolyzate

Example 1a): the cake proteins were extracted over a period of 1 hour at room temperature, i.e. at a temperature of 20° C., at pH 12, using an amount of 10% by weight of cake relative to the total weight of cake and water as solvent. The proteins thus extracted were subjected to hydrolysis for a period of 2 hours at a temperature of 55° C. and pH 8.5, with a volume concentration of 5% alcalase in liquid form relative to the total volume of alcalase and protein. The enzyme was inactivated by heating for a period of 20 minutes at a temperature of 90° C. and pH 6.5. The mixture was then cooled, centrifuged and filtered (0.22 μm).

Example 1b): the cake proteins were extracted over a period of one hour at room temperature, i.e. at a temperature of 20° C., at pH 8.5, using an amount of 10% by weight of cake relative to the total weight of cake and water as solvent. The proteins thus extracted were subjected to hydrolysis for a period of 2 hours at a temperature of 55° C. and pH 8.5, with a volume concentration of 5% alcalase in liquid form relative to the total volume of alcalase and protein. The enzyme was inactivated by heating for a period of 20 minutes at a temperature of 90° C. and pH 6.5. The mixture was then cooled, centrifuged and filtered (0.22 μm).

Example 1c): the cake proteins were extracted over a period of one hour at room temperature, i.e. at a temperature of 20° C., at pH 12, using an amount of 10% by weight of cake relative to the total weight of cake and water as solvent. The proteins thus extracted were subjected to hydrolysis for a period of 2 hours at a temperature of 55° C. and pH 8.5, with a volume concentration of 5% papain in liquid form relative to the total volume of papain and protein. The enzyme was inactivated by heating for a period of 20 minutes at a temperature of 90° C. and pH 6.5. The mixture was then cooled, centrifuged and filtered (0.22 μm).

Example 2. Total Protein Content of the Hydrolyzate According to the Invention and Peptide Molecular Weight Profile Analysis

Example 2a) Total Protein Assay

Materials and method: The protein content of the raw materials and extracts was estimated by determining the total nitrogen (Kjeldahl method) and multiplying the value obtained by a factor of 6.25 (N×6.25).

Results: the results are collated in Table 1 (protein content of *H. rhamnoides*) hydrolyzates).

TABLE 1

| | Hydro-lyzate 1a) | Hydro-lyzate 1b) | Hydro-lyzate 1c) |
|---|---|---|---|
| Dry extract (% in g/100 g water) | 3.84 | 3.44 | 2.72 |
| Protein content/DM (%) | 37.62 | 46.5 | 64.2 |
| Protein content in the native hydrolyzate (g/L) | 14.4 | 16.0 | 17.46 |
| Protein content in the concentrated hydrolyzate (g/L) | 18.81 | 23.25 | 32.1 |

Conclusion: The total protein content in the hydrolyzate according to Example 1a) is between 18 and 32 g/L protein (Table 1). The total protein content is between 37% and 65% of the dry matter.

Example 2b) Peptide Molecular Weight Profile Analysis

Materials and method: The molecular weight distribution of the peptides of the hydrolyzate as prepared according to Example 1a) was analyzed by gel permeation on a column (Superose® 12 10/300 GL, GE Healthcare Life Sciences). The molecular weights were determined after calibration of the column with protein molecules of known molecular weight.

Results: the results are collated in Table 2.

TABLE 2

| Percentage of peptides/total peptides | Hydrolyzate 1a) | Hydrolyzate 1a)' | Hydrolyzate 1a)" |
|---|---|---|---|
| MW > 500 kDa | 0.96 | 0.13 | 2.76 |
| 100 < MW < 500 kDa | 4.14 | 0.3 | 0.13 |
| 30 < MW < 100 kDa | 4.06 | 5.55 | 8.48 |
| 5 kDa < MW < 30 kDa | 18.25 | 33.54 | 34.00 |
| MW < 5 kDa | 72.58 | 60.49 | 46.92 |

Conclusion: the hydrolyzate as prepared according to Example 1a) comprises more than 70% of peptides with an MW less than 5 kDa.

Example 3. In Vitro Effects of the Hydrolyzate According to the Invention on the Biomechanical Properties of the Skin Appendages Materials and method: A reagent comprising 1.5% albumin, 2 mM iron, 5 mM EDTA, and 25 mM $H_2O_2$ hydrogen peroxide was placed in the presence or absence of *H. rhamnoides* hydrolyzate. Albumin is oxidized in the presence of $H_2O_2$. The oxidation reaction is catalyzed with iron. Monitoring of the catalysis of the oxidation reaction was performed in the absence of iron. The mixture was incubated at 37° C. for 1 day. The amount of tryptophan, dityrosine, pentosidine, and glycation products was measured by fluorescence (excitation/emission wavelengths: 280 nm/340 nm for tryptophan; 315 nm/410 nm for dityrosine; 335 nm/385 nm for pentosidine; 370 nm/440 nm for general glycation products).

Results: the results are collated in Tables 3 to 6.

Example 3a) Reduction in Glycation Products (AGEs)

TABLE 3

| | Albumin control with iron | Albumin and iron and *H. rhamnoides* hydrolyzate according to Ex. 1a) (0.01% w/v) | Albumin and iron and *H. rhamnoides* hydrolyzate according to Ex. 1a) (0.1% w/v) |
|---|---|---|---|
| MEAN (%) | 100 | 66.4 | 40.6 |
| SD | 5.5 | 1.5 | 2.8 |
| Deviation (%) vs control | — | −33.6 | −59.4 |
| p-value statistic vs control | | <0.001 | <0.001 |

Conclusion: The presence of iron catalyzes the albumin oxidation process in the presence of hydrogen peroxide and is accompanied by the formation of fluorescent glycation products. *H. rhamnoides* hydrolyzate at 0.01% and 0.1% (w/v) decreased the formation of these glycation products by over 28% at least.

Example 3b) Reduction in Tryptophan Degradation

TABLE 4

| | Albumin control without iron | Albumin control with iron | Albumin, iron and hydro-lyzate Ex. 1a) 0.01% (w/v) | Albumin, iron and hydro-lyzate Ex. 1a) 0.1% (w/v) |
|---|---|---|---|---|
| MEAN (%) | 606.23 | 100.00 | 149.04 | 200.51 |
| SD (%) | 8.21 | 8.29 | 2.11 | 1.97 |
| Deviation (%) | | | 49 | 101 |
| p-value statistic vs control (iron) | <0.001 | | <0.001 | <0.001 |

Conclusion: The addition of the hydrolyzate according to the invention reduced the degradation of tryptophan by at least 30% following the oxidation of albumin, showing its ability to reduce the oxidation of proteins and thus to maintain and/or increase the mechanical properties of skin appendages, notably of the hair.

Example 3c) Reduction in Dityrosine Formation

TABLE 5

| | Albumin control with iron | Albumin, iron and hydrolyzate Ex. 1a) 0.01% (w/V) | Albumin, iron and hydrolyzate Ex. 1a) 0.1% (w/V) |
|---|---|---|---|
| MEAN (%) | 100.00 | 59.98 | 38.49 |
| SD (%) | 3.91 | 1.12 | 0.54 |
| Deviation (%) | — | −40 | −62 |
| p-value statistic vs control (iron) | | <0.001 | <0.001 |

Conclusion: The addition of the hydrolyzate according to the invention reduced the formation of dityrosine by at least 35% following the oxidation of albumin, showing its ability to reduce the oxidation of proteins and thus to maintain and/or increase the mechanical properties of skin appendages, notably the hair.

Example 3d) Reduction in Pentosidine Formation

TABLE 6

| | Albumin control with iron | Albumin, iron and hydrolyzate Ex. 1a) 0.01% (w/v) | Albumin, iron and hydrolyzate Ex. 1a) 0.1% (w/v) |
|---|---|---|---|
| MEAN (%) | 100.00 | 57.58 | 31.99 |
| SD (%) | 5.24 | 1.09 | 1.20 |
| Deviation (%) | — | −42 | −68 |
| p-value statistic vs control (iron) | — | — | <0.05 |

Conclusion: The addition of the hydrolyzate according to the invention reduced the formation of dityrosine by at least 35% following the oxidation of albumin, showing its ability to reduce the oxidation of proteins and thus to maintain and/or increase the mechanical properties of skin appendages, notably the hair.

Example 3e) Reduction in a Glycation Intermediate: Schiff Bases

Materials and method: The hydrolyzate as prepared according to Example 1a) (0.01% or 0.1% final (w/v)) was added or not (Control) to a buffer solution (phosphate-buffered saline (PBS)) comprising copper (200 µM) and lipoprotein (100 µg/mL). The mixture was incubated for a period of 48 hours at a temperature of 37° C. The amount (mean %) of Schiff bases was measured by spectrometry (excitation wavelength 370 nm/emission wavelength 440 nm).
Result:

TABLE 7

| | LDL control + $Cu_{2+}$ | LDL, copper, hydrolyzate according to Ex. 1a) 0.01% (w/v) | LDL, copper, hydrolyzate according to Ex. 1a) 0.1% (w/v) |
|---|---|---|---|
| MEAN | 100 | 68.39 | 6.36 |
| SD (%) | 6.55 | 13.31 | 7.35 |
| p-value (Anova) vs. control | | <0.05 | <0.05 |

Conclusion: the hydrolyzate according to the invention reduced the appearance of Schiff bases by at least 11%.

Example 4. Increase in the Growth of Skin Appendages

Materials and method: A suspension composed of fibroblasts from the papilla of human hair follicles and basal culture medium, containing 0.05% v/v growth factor cocktail and the presence or absence of the *H. rhamnoides* hydrolyzate to be tested, was centrifuged for 5 minutes at 200×g to form aggregates. Control conditions were produced by adding 0.05% v/v growth factor cocktail (ethanol EtOH control) and adding capsaicin (10 µm) as a cell sensitizer (capsaicin control) to the basal culture medium. The aggregates were incubated at a temperature of 37° C. under controlled atmosphere (5% $CO_2$ and 95% relative humidity).

The aggregates were rinsed in buffered saline solution (PBS) and the cells were separated by incubation in a mixture of proteases (collagenase A, trypsin) with EDTA.

A portion of the suspended cells was taken up in PBS for flow cytometry analysis. The cell count and autofluorescence are the two parameters measured. Autofluorescence is a direct parameter easily measured and used as a marker of cell senescence (Rattan et al. 1982). The cell count is an indirect parameter of the growth potential of the hair follicle. Another portion of cells was used for analysis of the cell DNA content and ATP production rate. These two parameters were measured according to the suppliers' instructions (CyQuant NF Cell proliferation Assay Kit C35006, Invitrogen and Bioluminescence Assay Kit CLS II Roche 11699695001, Sigma-Aldrich).

Results: the results are collated in Tables 8 (effects of *H. rhamnoides* hydrolyzate on the amount of DNA in papilla fibroblasts grown as aggregates), 9 (effects of *H. rhamnoides* hydrolyzate on ATP production by papilla fibroblasts grown as aggregates) and 10 (effects of *H. rhamnoides* hydrolyzate on the number of papilla fibroblasts grown as aggregates, their granularity and autofluorescence measured by flow cytometry).

TABLE 8

| | MEAN | % deviation vs control | P value (Anova test n = 6) |
|---|---|---|---|
| EtOH control | 100 | — | P < 0.05 (T test) |
| Capsaicin control (10 µM) | 23 | −77 | |
| Capsaicin (10 µM) + hydrolyzate of Ex. 1a) 0.1% (w/v) | 141 | +41 | P < 0.05 |

Conclusion: Treatment of sensitized papilla fibroblast aggregates with capsaicin at a concentration of 10 µM reduced the amount of DNA in the cells. Co-addition of *H. rhamnoides* hydrolyzate at 0.03% (w/v) reduced the negative impacts of capsaicin, demonstrating the hydrolyzate's ability to reduce the loss of skin appendages, in particular of the hair. Treatment of the aggregates with *H. rhamnoides* hydrolyzate at 0.1% (w/v) increased the total amount of DNA (+41% relative to the control), demonstrating the effect of the hydrolyzate according to the invention on increasing the growth of skin appendages.

TABLE 9

| | MEAN | SD | % Activity | |
|---|---|---|---|---|
| EtOH control | 100 | 21 | — | P < 0.05 (t-test) |
| Capsaicin control (10 µM) | 24 | 3 | −76 | — |
| Capsaicin (10 µM) + hydrolyzate of Ex. 1a) 0.03% (w/v) | 154 | 17 | +54 | P < 0.001 (t-test) |

Conclusion: Treatment of sensitized papilla fibroblast aggregates with capsaicin at a concentration of 10 µM reduced the production of ATP in the cells by 76% relative to the control (ethanol). The combined addition to capsaicin of the *H. rhamnoides* hydrolyzate at 0.03% (w/v) made it possible 1) to counteract the negative impacts of capsaicin, thus demonstrating the ability of the hydrolyzate according to the invention to reduce the loss of skin appendages, advantageously of the hair, and 2) to stimulate the production of ATP by at least 16% relative to the non-sensitized control, showing the effect of said hydrolyzate on increasing the growth of the skin appendages, preferentially of the hair.

TABLE 10

| | Number of cells (%) | Granularity (%) | Autofluorescence (%) |
|---|---|---|---|
| Control (EtOH) | 100 | 100 | 100 |
| Capsaicin control (10 μM) | 28 | 217 | 235 |
| Capsaicin (10 μM) + hydrolyzate of Ex. 1a) 0.03% (w/v) | 127 | 130 | 97 |

Conclusion: Treatment of papilla fibroblast aggregates sensitized with capsaicin (10 μM) reduced the number of papilla fibroblasts, increased the overall granularity of the cells, and increased the fluorescence relative to the control (EtOH), this involving hair loss. The combined addition of *H. rhamnoides* hydrolyzate at 0.03% (w/v) to capsaicin reduced the negative impacts of capsaicin on the three measured parameters and boosted the cell count by 54% relative to the control, showing the ability of the hydrolyzate to reduce hair loss. In addition, the number of cells measured in the presence of the hydrolyzate was also greater than that of the control not sensitized with capsaicin, showing an effect on increasing the number of fibroblasts and thus an effect on hair growth. These results showed the protective potential of *H. rhamnoides* hydrolyzate against early or induced hair loss and a potential hair growth stimulator.

Example 5. Ex-Vivo Effect on Growth

Materials and method: Human follicles were cultured ex vivo in complete growth medium containing 0.5 μg/ml insulin, and treated with capsaicin at μM. The latter molecule is used as an agent causing slowing of follicle growth. A control condition without capsaicin treatment was produced. Capsaicin-sensitized follicles were treated or not with 0.03% (w/v) *H. rhamnoides* hydrolyzate. Each culture condition was evaluated on at least follicles cultured in isolation (n=10). The follicles were incubated at 37° C. in the presence of 5% $CO_2$. The culture medium was renewed three times a week for approximately 2 weeks. The elongation of the hair shafts of the cultured follicles was obtained from photographs taken on different days. The hair length was evaluated by image analysis (Image J) and presented in μm as a mean±standard error.

Results: the results are collated in Table 11 (hair elongation values (μm))

TABLE 11

| Day | Control MEAN (μm) | Control and capsaicin (10 μm) MEAN (μm) | Capsaicin (10 μm) and hydrolyzate Ex. 1a) 0.03% (w/v) MEAN (μm) | Treated versus untreated statistic (T-test) |
|---|---|---|---|---|
| 0 | 0 | 0 | 0 | >0.05 (not significant) |
| 6 | 1278 | 806 | 899 | <0.05 |
| 8 | 1492 | 861 | 962 | <0.01 |
| 11 | 1628 | 869 | 1009 | <0.01 |
| 13 | 1722 | 938 | 1072 | <0.01 |
| 15 | 1721 | 936 | 1048 | <0.01 |

Conclusion: Hair follicles cultured ex vivo in a medium containing 0.5 μg/ml insulin continued to grow, as evidenced by the hair shaft elongation (Control). Capsaicin (30 μM) treatment caused a noticeable loss in elongation by day 6 of culture relative to the control. Treatment of hair follicles, sensitized with capsaicin, with 0.03% (w/v) *H. rhamnoides* hydrolyzate significantly improved hair elongation as early as the sixth day of culture compared with capsaicin-treated follicles.

Example 6. Repairing Effect on Hair Fibers

Materials and method: Dark brown Caucasian hair locks were sized (1 g; 12 cm) and prepared for the study. The hair locks were washed and then bleached three times using a hydrogen peroxide solution (5.6% $H_2O_2$+13.9% $(NH_4)_2S_2O_8$, pH=9.4) for a period of 30 minutes. Healthy (unbleached) hair locks were kept as a control. After washing and drying for a period of 45 minutes at 55° C. under a flow of air, the hair locks were immersed for 24 hours in distilled water (as a control) or in an aqueous solution containing 1% *H. rhamnoides* hydrolyzate. Both solutions were buffered beforehand at pH 5.5. The locks were rinsed and then dried for 1 hour at about 60° C. under a flow of air. The denaturing temperature of the human proteins was determined by differential calorimetry (Wortmann et al. 1993) with a heating rate of 2 K/min and a differential enthalpy analyzer (DSC Q100, TA Instruments).

Results:

TABLE 12

| | Unbleached healthy hair | Control bleached hair | Bleached hair + hydrolyzate Ex. 1a) 1% (w/v) |
|---|---|---|---|
| Mean (° C.) | 140.4 | 132 | 135.5 |
| SD (° C.) | 0.07 | 0.09 | 0.21 |
| Deviation (° C.) | 8.4 | — | 3.5 |
| Repair index (%) | — | — | 41% |
| P value (Anova test n = 6) | <0.001 | — | <0.001 |

Conclusion: The hair bleached with hydrogen peroxide was more unstable than the healthy unbleached hair. The difference in the denaturing temperature of the hair fiber proteins was −8° C. between damaged and healthy hair. The difference in the denaturing temperature between peroxidized hair treated with *H. rhamnoides* hydrolyzate and the control hair was only −4.9° C. Treatment of the damaged hair improved the stability of the hair proteins against heat denaturing by +3.5° C. *H. rhamnoides* hydrolyzate showed a repairing effect on the hair fiber damaged with hydrogen peroxide.

Example 7: Examples of Compositions Comprising the Hydrolyzate According to the Invention

Example 7a): Shampoo

TABLE 13

| Phase | Name | Amount (% by total weight) |
|---|---|---|
| A | Water | 52.95 |
| A | Cocamidopropyl betaine | 9.46 |
| A | Cocoyl glucoside | 13.44 |
| A | Disodium laureth sulfosuccinate | 16.25 |
| A | Dicaprylyl ether, lauryl alcohol | 0.50 |
| A | Polyquaternium-7 | 1.0 |
| A | Sodium benzoate | 0.50 |

TABLE 13-continued

| Phase | Name | Amount (% by total weight) |
|---|---|---|
| B | Water | Qs 3.10 |
| B | Hydrolyzate according to Example 1a) | 0.1-2 |
| C | Fragrance | 0.05 |
| D | Polyethylene glycol/PPG-120/10 Trimethylolpropane | 1.50 |
| E | Citric acid | 1.25 |

The shampoo is prepared by the usual methods in the field well known to those skilled in the art, by mixing the four phases and adjusting the composition to a pH of 5.2 and to a viscosity of 2200 mPa·s (measured with a Brookfield instrument (RVT; 23° C., spindle 5; 50 rpm)).

Example 7b: Aqueous-Alcoholic Solution for the Scalp

TABLE 14

| Phase | Name | Amount (% by total weight) |
|---|---|---|
| A | Water | 84.35 |
| A | Chlorphenesin and methyl paraben | 0.30 |
| A | Xanthan gum | 0.10 |
| B | 96% ethanol | 10.00 |
| C | Water | Qs 3.25 |
| C | Hydrolyzate according to Example 1a) | 1-2 |

The aqueous-alcoholic solution is prepared by the usual methods in the field well known to those skilled in the art, by mixing the three phases and adjusting the composition to a pH of 6.2.

Example 7c: Mask for the Scalp

TABLE 15

| Phase | Name | Amount (% by total weight) |
|---|---|---|
| A | Polyquaternium-37, dicaprylyl carbonate, lauryl glucoside | 2.00 |
| A | Distearoylethyl hydroxyethylmonium methosulfate, cetearyl alcohol | 1.00 |
| A | Hydrogenated plant glyceride | 2.50 |
| A | Cetearyl alcohol | 3.00 |
| A | Dicaprylyl carbonate | 0.50 |
| B | Water | 87.05 |
| B | Sodium benzoate | 0.40 |
| C | Hydrolyzate according to Example 1a) | 2 |
| C | Water | 1.25 |
| D | Fragrance | 0.5 |
| D | Citric acid | qs |

The mask is prepared by the usual methods well known to those skilled in the art, by mixing the four phases and adjusting the composition to a pH of 4.1 and to a viscosity of 26 000 mPa·s (measured with a Brookfield instrument (RVT; 23° C., spindle 5; 50 rpm)).

Example 7d: Hair Serum

TABLE 16

| Phase | Name | Amount (% by total weight) |
|---|---|---|
| A | Water | 93.05 |
| A | Propylene glycol, phenoxyethanol, chlorphenesin, methylparaben | 2.50 |
| A | Glycerol | 1.00 |
| B | Xanthan gum | 0.20 |
| B | Sodium polyacrylate | 0.25 |
| C | Hydrogenated castor oil, coceth-7, PPG-1 PEG-9 lauryl glycol ether | 1.00 |
| C | Hydrolyzate according to Example 1a) | 2 |

The invention claimed is:

1. A cosmetic method comprising topically applying an effective amount of a composition comprising a hydrolysate of *Hippophae rhamnoides* cake to a skin appendage in need thereof, wherein said composition is applied in an effective amount for increasing the growth of skin appendages and/or decreasing the loss thereof; and/or for maintaining and/or increasing the biomechanical properties and/or the surface and/or textural properties of the skin appendages; and/or for repairing damaged skin appendages.

2. The method as claimed in claim 1, wherein the hydrolyzate is a hydrolyzate of the coproduct from the extraction of *Hippophae rhamnoides* seeds with supercritical $CO_2$ or of the coproduct obtained by pressing said seeds.

3. The method as claimed in claim 1, wherein the hydrolyzate is an enzymatic hydrolyzate.

4. The method as claimed in claim 1, wherein the hydrolyzate is obtained by enzymatic digestion at alkaline pH.

5. The method as claimed in claim 1, wherein the hydrolyzate contains:

a dry matter content of 2% to 10% by weight, a total protein content of from 15 g/L to 35 g/L of hydrolyzate, a percentage of peptides with a molecular weight of from 5 kDa to 30 kDa of between 15% and 40%, a percentage of peptides with a molecular weight of less than 5 kDa of between 40% and 85%.

6. The method as claimed in claim 1, wherein the cake hydrolyzate is present in the composition in an amount effective to reduce negative effects of aging of the skin appendages.

7. The method as claimed in claim 1 wherein the cake hydrolyzate is present in the composition in an amount effective to improve color and/or sheen and/or radiance and/or volume of the skin appendages.

8. The method as claimed in claim 1, wherein the cake hydrolyzate is included in the composition in a content of between $1\times10^{-4}$% to 10% by weight, relative to the total weight of the composition.

9. The method as claimed in claim 8, wherein the composition comprises at least one cosmetically acceptable excipient and in that this composition is chosen from a serum, a lotion, a cream, a shampoo, a hair conditioner, an oil, a milk, an ointment, a paste, a foam, an emulsion, a hydrogel, a shower gel, a mask, a lacquer, a spray, a wax, a mascara, a makeup pencil or a varnish, a conditioner, or a lotion.

10. The method as claimed in claim 9, wherein the hydrolyzate is a hydrolyzate of the coproduct from the extraction of *Hippophae rhamnoides* seeds with supercritical $CO_2$ or of the coproduct obtained by pressing said seeds.

* * * * *